US009969782B2

(12) United States Patent
Cardozo

(10) Patent No.: US 9,969,782 B2
(45) Date of Patent: May 15, 2018

(54) HIGHLY IMMUNOGENIC PEPTIDES DERIVED FROM THE HUMAN IMMUNODEFICIENCY VIRUS V2 REGION

(71) Applicant: New York University, New York, NY (US)

(72) Inventor: Timothy Cardozo, New York, NY (US)

(73) Assignee: New York University, New York, NY (US)

( * ) Notice: Subject to any disclaimer, the term of this patent is extended or adjusted under 35 U.S.C. 154(b) by 269 days.

(21) Appl. No.: 14/508,669

(22) Filed: Oct. 7, 2014

(65) Prior Publication Data

US 2015/0125476 A1    May 7, 2015

Related U.S. Application Data

(60) Provisional application No. 61/887,708, filed on Oct. 7, 2013.

(51) Int. Cl.
| | |
|---|---|
| *A61K 39/21* | (2006.01) |
| *C07K 14/28* | (2006.01) |
| *C07K 16/10* | (2006.01) |
| *A61K 39/12* | (2006.01) |
| *A61K 39/00* | (2006.01) |

(52) U.S. Cl.
CPC .............. *C07K 14/28* (2013.01); *A61K 39/12* (2013.01); *C07K 16/1063* (2013.01); *A61K 39/21* (2013.01); *A61K 2039/6037* (2013.01); *C07K 2317/21* (2013.01); *C07K 2317/34* (2013.01); *C07K 2317/76* (2013.01); *C07K 2319/33* (2013.01); *C07K 2319/55* (2013.01); *C12N 2740/16134* (2013.01)

(58) Field of Classification Search
CPC ................ C07K 16/1063; A61K 39/21; C12N 2740/16134
See application file for complete search history.

(56) References Cited

U.S. PATENT DOCUMENTS

| | | | |
|---|---|---|---|
| 6,815,201 B2 * | 11/2004 | Pinter ..................... | A61K 39/12 435/339.1 |
| 2013/0071424 A1 * | 3/2013 | Cardozo .................. | C07K 7/08 424/192.1 |

FOREIGN PATENT DOCUMENTS

WO    2012050893 A2    4/2012

OTHER PUBLICATIONS

Sullivan, N., et al., 1993, Effect of amino acid changes in the V1/V2 region of the human immunodeficiency virus type 1 glycoprotein on subunit association, syncytium formation, and recognition by neutralizing antibody, J. Virol. 67(6):3674-3679.*
Mayr, L. M., et al., 2013, Epitope mapping of conformational V2-specific anti-HIV human monoclonal antibodies reveals an immunodominant site in V2, PLOS ONE, 8(7):e70859 (1-9).*
McLellan et al., "Structure of HIV-1 gp120 V1/V2 Domain with Broadly Neutralizing Antibody PG9," Nature 480:336-343 (2011).
Kayman et al., "Presentation of Native Epitopes in the V1/V2 and V3 Regions of Human Immunodeficiency Virus Type 1 gp120 by Fusion Glycoproteins Containing Isolated gp120 Domains," J. Virol. 68(1):400-410 (1994).
Rerks-Ngarm et al., "Vaccination with ALVAC and AIDSVAX to Prevdent HIV-1 Infection in Thailand," N. Engl. J. Med. 361(23):2209-2220 (2009).

* cited by examiner

*Primary Examiner* — Jeffrey Parkin
(74) *Attorney, Agent, or Firm* — LeClairRyan PLLC

(57) ABSTRACT

The present invention relates to an isolated immunogenic peptide chimera comprising a first peptide moiety comprising the amino acid sequence of SEQ ID NO: 1, or at least a contiguous 5 amino acid fragment thereof, a second peptide moiety comprising the amino acid sequence of SEQ ID NO: 2, or at least a contiguous 5 amino acid fragment thereof, and a linker joining the first and second peptide moieties, wherein the first peptide moiety is at the immunogenic peptide chimera's N-terminus and the second peptide moiety is at the immunogenic peptide chimera's C-terminus. Also disclosed is an immunogenic peptide including the amino acid sequence corresponding to SEQ ID NO: 6, or at least a contiguous 5 amino acid fragment thereof, having a length sufficient to form β-hairpin structure. A further aspect of the present invention is an immunogenic peptide including the amino acid sequence corresponding to SEQ ID NO: 15, or at least a contiguous 5 amino acid fragment thereof, capable of folding into an alpha-helical structure. These immunogenic peptides can be inserted into an immunogenic scaffold protein to form an immunogenic polypeptide. The immunogenic peptides or immunogenic polypeptides can be used in an immunogenic vaccine composition and in methods of inducing a neutralizing antibody response, or inducing a protective and non-neutralizing antibody response, or protective antibodies, against HIV-1 gp120 in a subject. Isolated antibodies and methods of detecting are also disclosed.

11 Claims, 7 Drawing Sheets

FIG. 4A

HIGHLY IMMUNOGENIC PEPTIDES DERIVED FROM THE HUMAN IMMUNODEFICIENCY VIRUS V2 REGION

This application claims the benefit of U.S. Provisional Patent Application Ser. No. 61/887,708, filed Oct. 7, 2013, which is hereby incorporated by reference in its entirety.

This invention was made with government support under grant numbers 1RO1 AI084119 and 1DP1 DA036478 awarded by the National Institutes of Health. The government has certain rights in this invention.

FIELD OF THE INVENTION

The present invention relates to immunogenic peptides and polypeptides for protection against HIV infection.

BACKGROUND OF THE INVENTION

Human Immunodeficiency Virus-1 (HIV-1) infection has been reported throughout the world in both developed and developing countries. HIV-2 infection is found predominately in West Africa, Portugal, and Brazil. At the end of 2008, an estimated 1,178,350 persons aged 13 and older were living with HIV infection in the United States. Of those, 20% had undiagnosed HIV infections (CDC, "HIV Surveillance—United States, 1981-2008," *MMWR* 60(21); 689-693 (2008)).

The HIV viruses are members of the Retroviridae family and, more particularly, are classified within the Lentivirinae subfamily. Like nearly all other viruses, the replication cycles of members of the Retroviridae family, commonly known as the retroviruses, include attachment to specific cell receptors, entry into cells, synthesis of proteins and nucleic acids, assembly of progeny virus particles (virions), and release of progeny viruses from the cells. A unique aspect of retrovirus replication is the conversion of the single-stranded RNA genome into a double-stranded DNA molecule that must integrate into the genome of the host cell prior to the synthesis of viral proteins and nucleic acids.

HIV encodes a number of genes including three structural genes—gag, pol, and env—that are common to all retroviruses. The envelope protein of HIV-1 is a glycoprotein of about 160 kd (gp160). During virus infection of the host cell, gp160 is cleaved by host cell proteases to form gp120 and the integral membrane protein, gp41. The gp41 portion is anchored in the membrane bilayer of the virion, while the gp120 segment protrudes into the surrounding environment. The membrane bilayer of the virion is derived from human host cells and therefore is immunologically silent, so gp120 is the major target for host antibodies on the virion. gp120 and gp41 are non-covalently associated, and free gp120 can be released from the surface of virions and infected cells. The gp120 polypeptide is also instrumental in mediating entry into the host cell.

Historically, viral vaccines have been enormously successful in the βprevention of infection by a particular virus. Therefore, when HIV was first isolated, there was a great amount of optimism that an HIV vaccine would be developed quickly. However, this optimism quickly faded, because a number of unforeseen problems emerged, and to date an efficacious HIV vaccine has not been produced as a marketable product anywhere in the world.

It is widely thought that a successful vaccine should be able to induce a strong antibody response against diverse HIV-1 strains. Antibodies, by attaching to the incoming virions, can reduce or even prevent their infectivity for target cells and possibly prevent the cell-to-cell spread of virus in tissue. There have only been three HIV vaccine randomized placebo controlled clinical trials to date, and the first two (VaxGen and STEPS) failed to protect against HIV acquisition. The failure of the Vaxgen HIV vaccine trial demonstrated that whole gp120 protein molecules alone could not serve as vaccine immunogens that protect against HIV acquisition. The failure of the STEPS HIV vaccine demonstrated that cellular immunity stimulating vaccines utilizing non-gp120-encoding determinants are not protective. The success of the third trials, RV144, showed that certain, but not all, antibodies targeted at the V1/V2 domain of gp120 could protect against HIV acquisition. Thus, there remains a need for synthetic immunogens that mimic epitopes in the V1V2 domain that can elicit an immunological response in a subject against multiple HIV strains and subtypes that exhibits features of the antibodies in the RV144 trial that protected from HIV infection, for example when administered as a vaccine.

A prior filing (U.S. patent application Ser. No. 13/612,300 to Cardozo) teaches a series of peptide immunogens derived from the V2 loop of gp120 that react specifically with serum immunoglobulins from the human subjects vaccinated in the RV144 trial. However, it is not known whether these peptides contain the epitopes targeted by the specific antibodies that protected against HIV infection as most or all subjects had serum immunoglobulins reacting with these peptides, but only very few were protected from HIV infection. One feature of the protective antibodies is that they cross-react with V1V2 domains from several HIV subtypes, including subtypes AE and B. Antibodies elicited in any mammal by vaccination with any known molecule have never been shown to cross react between the V1V2 domains of several HIV subtypes, therefore antibodies with this same property as the protective antibodies detected in humans in the RV144 trial have never been elicited in mammals prior to the present invention. As the diversity of specificities of antibodies produced by the human immune system is virtually infinite, it would not have been apparent to a skilled scientist how to elicit, by vaccination in any mammal, antibodies that cross-react with V1V2 domains from several HIV subtypes, including subtypes AE and B.

The present invention is directed to overcoming deficiencies of prior approaches to addressing HIV infection.

SUMMARY OF THE INVENTION

The present invention relates to an isolated immunogenic peptide chimera comprising a first peptide moiety comprising the amino acid sequence of SEQ ID NO: 1, or at least a contiguous 5 amino acid fragment thereof, a second peptide moiety comprising the amino acid sequence of SEQ ID NO: 2, or at least a contiguous 5 amino fragment thereof, and a linker joining the first and second peptide moieties, wherein said first peptide moiety is at said immunogenic peptide chimera's N-terminus and said second peptide moiety is at said immunogenic peptide chimera's C-terminus.

Another aspect of the present invention relates to an isolated immunogenic peptide comprising the amino acid sequence corresponding to SEQ ID NO: 6, or at least a contiguous 5 amino acid fragment thereof, having a length sufficient to form β-hairpin structure.

Another aspect of the present invention relates to an isolated immunogenic peptide comprising the amino acid sequence corresponding to SEQ ID NO: 15, or at least a contiguous 5 amino acid fragment thereof, capable of folding into an alpha-helical structure.

Other aspects of the present invention relate to an isolated immunogenic polypeptide comprising the immunogenic peptide inserted into an immunogenic scaffold protein, a vaccine composition comprised of the immunogenic peptide and an immunologically or pharmaceutically acceptable vehicle or excipient, isolated antibodies, methods of detecting HIV, as well as methods of inducing any of a neutralizing antibody response, a protective and non-neutralizing antibody response, and protective antibodies, all against HIV-1.

The holy grail of HIV vaccine research is a molecular correlate of protection from HIV infection in human subjects. At present, direct detection of any such correlate must derive solely from data recorded in the RV144 HIV vaccine trial, because this is the only clinical vaccine trial in the history of HIV vaccine research to show efficacy in preventing HIV infection in humans. Furthermore, conclusions about protection can only derive from data in the RV144 immune correlates case control analysis, among the various pilot and sub-analysis data emerging from the trial. Using only the data from the RV144 case control analysis, the inventors determined that the most likely molecular correlate of protection from HIV infection detected in the RV144 trial is a human antibody targeting a peptide (non-glycan) epitope located between positions 165 and 181 of the V2 loop of the surface envelope glycoprotein of the HIV virus that is conserved between HIV subtypes AE and B. In the present invention, evidence is presented that this specific segment is immunogenic in humans, rabbits, and in mice. Finally, it is shown that a focused immunogen with only this segment on a non-HIV protein scaffold can elicit cross-subtype anti-gp120 serum antibodies by vaccination in a mammal. Such an immunogen could be a critical component for an efficacious HIV vaccine.

BRIEF DESCRIPTION OF THE DRAWINGS

FIGS. 4A-4C show immunofocusing to $V2^{165-181}$ FIG. 4A shows a model of gp120 trimer integrating a cryo-EM model of the trimer (PDB code 3DNO (Liu et al., "Molecular Architecture of Native HIV-1 gp120 Trimers," *Nature* 455: 109-113 (2008), which is hereby incorporated by reference in its entirety)) with the crystallographic structure of the V1V2 domain (PDB code: 3U1S (McLellan et al., "Structure of HIV-1 gp120 V1/V2 Domain With Broadly Neutralizing Antibody PG9," *Nature* 480: 336-343 (2011), which is hereby incorporated by reference in its entirety)). The proteins are shown in ribbon diagram with the gp120 core colored grey, the V1V2 domain colored yellow and $V2^{165-181}$ colored purple. Only the β-hairpin containing a sequence designed as claimed in this invention to mimic the properties of $V2^{165-181}$ is spliced out and fused to a non-HIV protein scaffold, cholera toxin B (CTB; green ribbon). This produces a $V2^{165-181}$ immunofocused immunogen ($CTB^{165-181}$), which was used as the protein boost to immunize rabbits via a heterologous DNA prime-protein boost protocol previously used (Zolla-Pazner et al., "Cross-Clade HIV-1 Neutralizing Antibodies Induced With V3 Scaffold Protein Immunogens Following Priming With gp120 DNA," *J. Virol.* 85: 9887-9898 (2011), which is hereby incorporated by reference in its entirety). As shown in FIG. 4B, the sera from rabbits immunized with the $V2^{165-181}$ immunofocused immunogen exhibit antibodies that specifically neutralize strains from multiple HIV subtypes. Each strain is named with the subtype first followed by a dash and then the specific strain name. Numbers are the geomean titers of the sera from four rabbits in each group in the TZM.b1 neutralization assay for 50% neutralization ($NT_{50}$) of the indicated strains. The second column is the control immunization with the same DNA prime and the wild-type CTB protein (wtCTB) without the V2$^{165-181}$ insert. The titers prove that the sera contains V2$^{165-181}$-specific antibodies that recognize V2$^{165-181}$ on native virions and cross react between multiple subtypes. FIG. 4C shows ELISA binding of serum IgG from the same rabbits to V1V2 domains scaffolded on a non-HIV gp70 scaffold. The gp70-V1V2 fusion protein exhibiting the V1V2 domain from the Case A2 strain of HIV (from Glade/subtype B), reactivity with which is shown at the far right of FIG. 4C, is the exact protein used to detect protective antibodies in the RV144 immune correlates analysis of Haynes et al, "Immune-Correlates Analysis of an HIV-1 Vaccine Efficacy Trial," *NEJM* 366: 1275-1286 (2012), which is hereby incorporated by reference in its entirety. To measure cross-reactivity typical of protective antibodies, a gp70-V1V2 fusion protein exhibiting the V1V2 domain from Glade/subtype E strain A244 was also tested in FIG. 4C, middle panel. As a control, the rabbit serum was also tested against full-length gp120 from the Glade/subtype E strain A244. Blue bars represent the reactivity of the rabbit serum obtained after immunization from the experiment with the above described proteins. Red bars represent the serum obtained before immunization, as a control. The X-axis displays the immunogens used to immunize the rabbits: CTB+P1 and P2 refer to two different designs of the CTB-V2$^{165-181}$ immunogen, while "CTB" refers to a control immunization of the rabbits with the unaltered wild-type CTB protein alone, which contains no HIV antigen. The immunization was performed with a DNA prime, protein boost protocol, which was previously taught in U.S. patent application Ser. No. 13/612,300 to Cardozo, which is hereby incorporated by reference in its entirety. The DNA prime consisted of the codon-optimized DNA sequence from the Glade/subtype E strain 93TH976.17, as previously taught in Wang et. al "Cross-Subtype Antibody and Cellular Immune Responses Induced by a Polyvalent DNA Prime-Protein Boost HIV-1 Vaccine in Healthy Human Volunteers," *Vaccine* 26:2947-3957 (2008), which is hereby incorporated by reference in its entirety. FIG. 4C shows that anti-V2 antibodies were not elicited by the DNA prime, as the reactivity seen with gp120 is not present against gp70-V1V2. Thus, all anti-V1V2 antibodies must have been elicited by the immunogens claimed in the present invention. In addition, these anti-V1V2 antibodies are shown in FIG. 4C to react with gp70-V1V2-CaseA2 and with gp70V1V2-A244, which is the exact profile of the protective antibodies observed in the RV144 HIV vaccine clinical trial. FIG. 4C thereby demonstrates that a novel immunogen was designed that elicits anti-V2$^{165-181}$ antibodies in a mammal/rabbit that mirror the properties observed by protective antibodies elicited in the RV144 clinical trial.

DETAILED DESCRIPTION OF THE INVENTION

Figure 1:
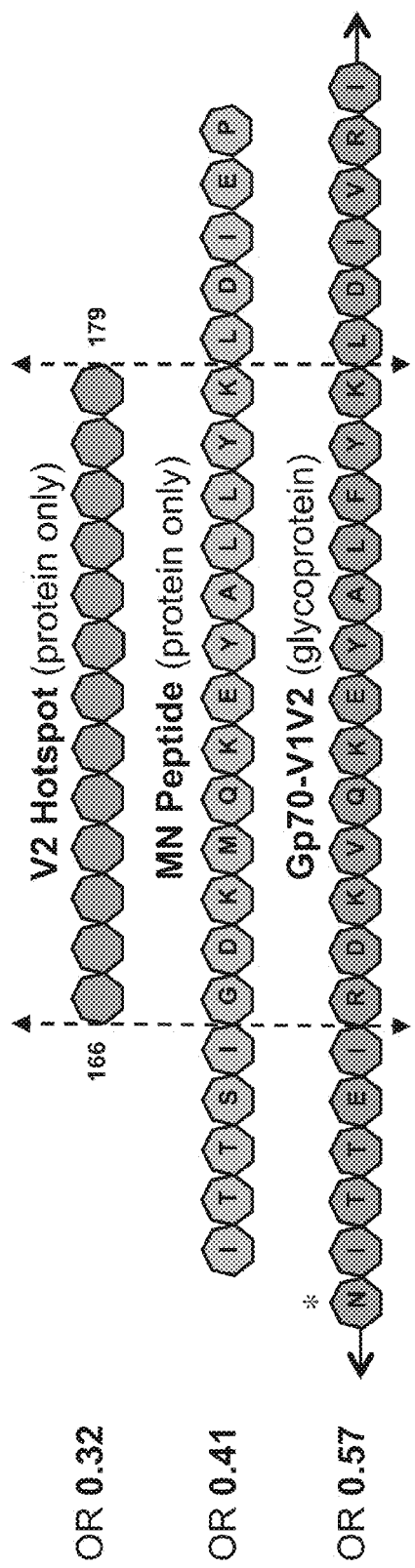
FIG. 1 shows that protection maps to $V2^{165-181}$. Of the approximate 270 assays performed in the RV144 immune correlates analysis, only antibodies binding three reagents showed an Odds Ratio (OR) of 0.57 or lower (OR shown at the left of FIG. 1). These reagents were the gp70-V1V2 fusion glycoprotein (sequence for a portion of the V1V2 domain of gp70 shown in blue heptagons with glycosylation sites indicated by an asterisk), the MN peptide (sequence shown as green heptagons from position 161-183), and the V2 hotspot (shown as purple heptagons spanning positions 166-179). All three of these reagents include an unglycosylated portion of the V2 domain spanning positions 166-179. The two positions found to be associated with vaccine efficacy in the sieve analysis of Rolland et al., "Increased HIV-1 Vaccine Efficacy Against Viruses With Genetic Signatures in Env V2," *Nature* 490: 417-420 (2012), which is hereby incorporated by reference in its entirety, are positions 169 and 181 according to the numbering in the figure.

The present invention relates to an isolated immunogenic peptide chimera comprising a first peptide moiety comprising the amino acid sequence of SEQ ID NO: 1, or at least a contiguous 5 amino acid fragment thereof, a second peptide moiety comprising the amino acid sequence of SEQ ID NO: 2, or at least a contiguous 5 amino acid fragment thereof, and a linker joining the first and second peptide moiety, wherein said first peptide moiety is at said immunogenic peptide chimera's N-terminus and said second peptide moiety is at said immunogenic peptide chimera's C-terminus.

In accordance with this aspect of the present invention, the amino acid of SEQ ID NO: 1 has the following sequence: $X_1X_2X_3X_4X_5X_6X_7X_8X_9X_{10}X_{11}X_{12}X_{13}X_{14}X_{15}X_{16}$, where $X_1$ is K, R, T, Q or E; $X_2$ is Q, K, R, V, T, M, I, L, F, or E; $X_3$ is Q, K, R, V, E, T or H; $X_4$ is K, Q, R, N, T, E, or I; $X_5$ is V, A, I, E, D, Q, T, N, F, K, or G; $X_6$ is Y, H, R, N, S, Q, or F; $X_7$ is A, S, or T; $X_8$ is L, I, F, T, Y, or V; $X_9$ is F, L, or T; $X_{10}$ is Y, N, H, D, S, or V; $X_{11}$ is K, R, T, M, N, S, E, Q, V, or A; $X_{12}$ is L, P, Y, S, I, F, V, T, H, or G; $X_{13}$ is D, N, E, or V; $X_{14}$ is V, I, T, or L; $X_{15}$ is V, I, E, T, M, or A; and $X_{16}$ is Q, P, S, K, E, R, or A and the amino acid of SEQ ID NO: 2 has the following sequence: $X_1X_2X_3X_4X_5X_6X_7X_8X_9X_{10}X_{11}$, where $X_1$ is R, K, S, I, M, T, or Q; $X_2$ is N, K, or C; $X_3$ is C, N, R, or F; $X_4$ is T, C, or S; $X_5$ is F or S; $X_6$ is N, K, F, S, D, or Y; $X_7$ is M, V, I, N, T, or A; $X_8$ is T, I, S, V, or A; $X_9$ is T, S, A, P, or G; $X_{10}$ is E, V, L, S, N, T, G, D, E, R, I, V, A, or P; and $X_{11}$ is L, I, V, M, S, R, T, or N. Examples of specific first peptide moieties in accordance with the present invention include the following amino acid sequences: KMQKVYALTYKL-DIV (SEQ ID NO: 3) and KIQIVYALFYQLDIV (SEQ ID NO: 4). An exemplary second peptide moiety in accordance with the present invention is SFNITG (SEQ ID NO: 5). A further immunogenic peptide corresponding to this aspect of the present invention is the amino acid sequence SNNT-TESINIGPDKKQAVTGEIIGDIR (SEQ ID NO: 13).

The linker can be of natural origin, such as a sequence determined to exist in random coil between two domains of a protein. Alternatively, the linker can be of synthetic origin. For instance, the sequence (Gly4Ser)3 can be used as a synthetic unstructured linker.

Another aspect of the present invention relates to an isolated immunogenic peptide comprising the amino acid sequence corresponding to SEQ ID NO: 6, or at least a contiguous 5 amino acid fragment thereof, having a length sufficient to form a β-hairpin structure.

In accordance with this aspect of the present invention, the amino acid of SEQ ID NO: 6 has the following sequence:

$X_1X_2X_3X_4X_5X_6X_7X_8X_9X_{10}X_{11}X_{12}X_{13}X_{14}X_{15}X_{16}X_{17}X_{18}X_{19}AX_{20}X_{21}X_{22}$, where $X_1$ is R, K, S, I, M, T, or Q; $X_2$ is N, K, or C; $X_3$ is C, N, R, or F; $X_4$ is S, T, or C; $X_5$ is F or S; $X_6$ is N, K, F, S, D, or Y; $X_7$ is M, V, I, N, T, or A; $X_8$ is T, I, S, V, or A; $X_9$ is T, S, A, P, or G; $X_{10}$ is E, V, L, S, N, T, G, D, E, R, I, V, A, or P; $X_1$ is L, I, V, M, S, R, T, or N; $X_{12}$ is R, K, T, I, Q, S, A, G, or N; $X_{13}$ is D, N, K, G, or R; $X_{14}$ is K, R, T, E, Q, or I; $X_{15}$ is K, Q, R, T, V, M, I, L, F, or E; $X_{16}$ is Q, K, R, V, T, E, or H; $X_{17}$ is K, Q, R, N, T, or E; $X_{18}$ is V, A, I, E, D, Q, T, N, F, K, or G; $X_{19}$ is Y, H, R, S, N, Q, or F; $X_{20}$ is L, I, F, T, Y, or V; $X_{21}$ is F or L; and $X_{22}$ is Y, N, H, D, or S. In accordance with this aspect of the present invention, suitable isolated immunogenic peptides include peptides of the amino acid sequence of SFNITTSI-GDKMQKE (SEQ ID NO: 7), SFNMTTELRDKKQKV (SEQ ID NO: 8), SFNITTSIGDKMQQV (SEQ ID NO: 9), SFNMTTELGDKKQQV (SEQ ID NO: 10), SFNMT-TELQNQKQQV (SEQ ID NO: 11), SFNITTSLQNK-KQQV (SEQ ID NO; 12), and SFNITTSIGDKMQKV (SEQ ID NO: 14).

Another aspect of the present invention relates to an isolated immunogenic peptide comprising the amino acid sequence corresponding to SEQ ID NO: 15, or at least a contiguous 5 amino acid fragment thereof, capable of folding into an alpha-helical structure.

In accordance with this aspect of the present invention, the amino acid of SEQ ID NO: 15 has the following sequence: $X_1X_2DKX_3X_4X_5X_6X_7ALFYX_8LDX_9$, where $X_1$-$X_8$ is any natural or unnatural amino acid and $X_9$ is V or I. Suitable isolated immunogenic peptides include peptides of the amino acid sequence of DKYQQQQALFYQLD (SEQ ID NO: 16); DKMQKEYALLYKLD (SEQ ID NO: 17); DKQQQSQALFYQLD (SEQ ID NO: 18); DKQQQQSALFYQLD (SEQ ID NO: 19); DKSQQQQAL-FYQLD (SEQ ID NO: 20); DKQQQQQALFYQLD (SEQ ID NO: 21); DKQQQQQALFYSLD (SEQ ID NO: 22); DKQSQQQALFYQLD (SEQ ID NO: 23); or DKQQSQQALFYQLD (SEQ ID NO: 24).

The present invention also relates to an isolated immunogenic polypeptide of the present invention comprising the isolated immunogenic peptides described above and an immunogenic scaffold protein. The polypeptide has a conformation that is recognized by, and bound by, a neutralizing anti-HIV-1 antibody.

As used herein, a "neutralizing" antibody or antibody response is an antibody or response that results in binding and neutralization of at least one group of heterologous HIV-1 viruses that are members of a different subtype or clade than that of the source of the immunizing antigen. The scaffold protein can be one that is highly immunogenic and capable of enhancing the immunogenicity of any heterologous sequences fused to/inserted in it. According to certain embodiments of the present invention, the scaffold protein is cholera toxin subunit B (CTB). The scaffold protein may also be a homologue thereof which shares at least 50%, 60%, 70%, 80%, 90%, or 95% amino acid sequence identity with CTB, or a fragment or conservative amino acid substitution variant thereof, which homologue fragment or variant retains the immunogenicity and GM1-binding properties of CTB.

CTB is highly immunogenic and has been used in fusion constructs to enhance immunogenicity of its fusion partner polypeptide or peptide (McKenzie et al., "Cholera Toxin B Subunit as a Carrier to Stimulate a Mucosal Immune Response," *J. Immunol.* 133:1818-1824 (1984); Czerkinsky et al., "Oral Administration of a Streptococcal Antigen Coupled to Cholera Toxin B Subunit Evokes Strong Antibody Responses in Salivary Glands and Extramucosal Tissues," *Infect. Immun.* 57:1072-1077 (1989), each of which is hereby incorporated by reference in its entirety). CTB has also been described as a mucosal adjuvant for vaccines (Areas et al., "Expression and Characterization of Cholera Toxin B-Pneumococcal Surface Adhesin A Fusion Protein in *Escherichia Coli*: Ability of CTB-PsaA to Induce Humoral Immune Response in Mice," *Biochem. Biophys. Res. Commun.* 321:192-196 (2004), which is hereby incorporated by reference in its entirety).

An important factor for the immunogenic property of CTB is binding to GM1 ganglioside, which is present on the surface of mucosal cells. This results in its propensity to induce mucosal immunity and is highly desirable for an HIV immunogen or vaccine, because infection commonly occurs via a mucosal route. In addition, the availability of structural information of these proteins allows protein design that avoids or minimizes disruption of the GM1 binding site, thereby preserving the inherent immunogenicity of these polypeptides.

Other useful scaffolds for the construct of the present invention include a family of closely related bacterial proteins which are homopentamers of relatively small subunits (~100 aa). It is preferred that the scaffold protein be one that, like CTB, is highly immunogenic and capable of enhancing the immunogenicity of any heterologous sequences fused to or inserted in it (whether internally or at either terminus).

Another preferred scaffold protein in one that, like CTB, includes a binding site for the oligosaccharide portion of ganglioside GM1 in membranes. X-ray analysis of CTB revealed an oligosaccharide binding site formed by residues E51, Q56, H57, Q61, W88, N90, K91 (Sixina et al., "Lactose Binding to Heat Labile Enterotoxin Revealed by X-Ray Crystallography," *Nature* 355:561-64 (1992), which is hereby incorporated by reference in its entirety).

Other polypeptides, such as *E. coli* enterotoxin, that share the advantageous properties of CTB are also intended within the scope of the present invention as scaffolds for various isolated immunogenic polypeptides of the present invention to produce a neutralizing antibody response in vivo. One example of an *E. coli* enterotoxin useful as a scaffold protein herein is heat-labile enterotoxin B subunit, also referred to as LTc B (GenBank Accession No. AAC60441, which is hereby incorporated by reference in its entirety).

In accordance with this aspect of the present invention, the immunogenic peptide can be inserted directly into the scaffold's tertiary structure. This yields a polypeptide in which an exceptionally high fraction of the molecular surface presents V2 epitopes that are recognized by broadly-reactive neutralizing anti-gp120 antibodies and can elicit anti-HIV-1 antibody responses that preferably are broadly-reactive and neutralize the virus. Molecular modeling is used to test in-silico, whether various insertion positions in the scaffold and different loop lengths result in loop conformations that present the epitopes. Specifically, there are two approaches. Firstly, the scaffold is scanned for amino-acid positions that can be superimposed on the termini of the loop as observed in the V2/antibody complex. When superposition within small tolerances (<0.5 .ANG. root mean square deviation (RMSD) for the terminal residues is achieved, the model is evaluated for the absence of clashes with the scaffold structure. Secondly, the loop is inserted in a random conformation and subjected to conformational sampling. Low energy conformations generated during sampling are compared to the desired V2 conformation as observed in the V2/antibody complex. Sampling is over a restricted energy range. When the construct is such that conformations within 1.0 .ANG. backbone RMSD of the desired V2 conformation are identified in the simulation, a model of the immunogen-antibody complex is built to ensure that the scaffold does not interfere with the V2 loop/antibody binding.

The one or more peptides in the present invention can be synthesized by solid phase or solution phase peptide synthesis, recombinant expression, or can be obtained from natural sources. Automatic peptide synthesizers are commercially available from numerous suppliers, such as Applied Biosystems, Foster City, Calif. Standard techniques of chemical peptide synthesis are well known in the art (see e.g., SYNTHETIC PEPTIDES:A USERS GUIDE 93-210 (Gregory A. Grant ed., 1992), which is hereby incorporated by reference in its entirety). Peptide production via recombinant expression can be carried out using bacteria, such as *E. coli*, yeast, insect cells or mammalian cells and expression systems. Procedures for recombinant protein/peptide expression are well known in the art and are described by Sambrook et al., *Molecular Cloning: A Laboratory Manual* (C.S.H.P. Press, NY 2d ed., 1989), which is hereby incorporated by reference in its entirety.

Recombinantly expressed peptides can be purified using any one of several methods readily known in the art, including ion exchange chromatography, hydrophobic interaction chromatography, affinity chromatography, gel filtration, and reverse phase chromatography. The peptide is preferably produced in purified form (preferably at least about 80% to 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Another aspect of the present invention is directed to an immunogenic vaccine composition comprising the isolated immunogenic peptides or polypeptides described above, and an immunologically and pharmaceutically acceptable vehicle or excipient.

Suitable vehicles and excipients are described in REMINGTON'S PHARMACEUTICAL SCIENCE (19th ed., 1995), which is hereby incorporated by reference in its entirety. The incorporation of such immunologically and pharmaceutically acceptable components depends on the intended mode of administration and therapeutic application of the pharmaceutical composition. Typically, however, the vaccine composition will include a pharmaceutically-acceptable, non-toxic carrier or diluent, which are defined as vehicles commonly used to formulate pharmaceutical compositions for animal or human administration. The diluent is selected so as not to affect the biological activity of the composition. Exemplary carriers or diluents include distilled water, physiological phosphate-buffered saline, Ringer's solutions, dextrose solution, and Hank's solution.

Vaccine compositions can also include large, slowly metabolized macromolecules such as proteins, polysaccharides such as chitosan, polylactic acids, polyglycolic acids and copolymers (such as latex functionalized sepharose, agarose, cellulose), polymeric amino acids, amino acid copolymers, and lipid aggregates (such as oil droplets or liposomes).

The vaccine composition of the present invention may also be supplemented with an immunostimulatory cytokine. Preferred cytokines are GM-CSF (granulocyte-macrophage colony stimulating factor), interleukin 1, interleukin 2, interleukin 12, interleukin 18, or interferon-gamma.

The vaccine composition of the present invention can further contain an adjuvant. One class of preferred adjuvants is aluminum salts, such as aluminum hydroxide, aluminum phosphate, or aluminum sulfate. Such adjuvants can be used with or without other specific immunostimulating agents such as MPL or 3-DMP, QS-21, flagellin, polymeric or monomeric amino acids such as polyglutamic acid or polylysine, or pluronic polyols. Oil-in-water emulsion formulations are also suitable adjuvants that can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™, or other bacterial cell wall components). A suitable oil-in-water emulsion is MF59 (containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.) as described in WO90/14837 to Van Nest et al., which is hereby incorporated by reference in its entirety. Other suitable oil-in-water emulsions include SAF (containing 10% Squalene, 0.4% Tween 80, 5% pluronic-blocked polymer L121, and thr-MDP, either microfluidized into a submicron emulsion or vortexed to generate a larger particle size emulsion) and Ribi™ adjuvant system (RAS; containing 2% squalene, 0.2% Tween 80, and one or more bacterial cell wall components). Another class of suitable adjuvants are saponin adjuvants, such as Stimulon™ (QS-21) or particles generated therefrom such as ISCOMs (immunostimulating complexes) and ISCOMATRIX. Other suitable adjuvants include incomplete or complete Freund's Adjuvant (IFA). Such adjuvants are generally available from commercial sources.

Compositions of the present invention can be administered by parenteral, topical, intravenous, oral, subcutaneous, intraperitoneal, intranasal, or intramuscular means. The most typical route of administration for compositions formulated to induce an immune response is subcutaneous, although others can be equally effective. The next most common is intramuscular injection. This type of injection is most typically performed in the arm or leg muscles. Intravenous injections as well as intraperitoneal injections, intra-arterial, intracranial, or intradermal injections are also effective in generating an immune response.

The compositions of the present invention may be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Vaccine formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the vaccine of the present invention systemically, it may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Another aspect of the present invention relates to a method of inducing a neutralizing antibody response against a V2 epitope of HIV-1 gp120 in a subject. This method comprises administering to the subject the isolated immunogenic peptides or polypeptides, described above, under conditions effective to induce, in the subject, a neutralizing antibody response against the V2 epitope of the HIV-1 gp120. In a further embodiment of this aspect of the present invention, an HIV-1 positive subject is selected for administration of the isolated immunogenic peptides or polypeptides.

In accordance with this aspect of the present invention, a neutralizing antibody response is an antibody response that results in binding and neutralization of at least one group of heterologous HIV-1 viruses that are members of a different subtype or Glade than that of the source of the immunizing antigen. Such a response is an active response induced by administration of the immunogenic peptide or polypeptide and represents a means for vaccination against HIV-1.

In carrying out this aspect of the present invention, the above-described modes of administering and formulating can be used.

An MT-2 assay can be performed to measure neutralizing antibody responses. Antibody-mediated neutralization of selected strains or isolates of HIV-1 can be measured in an MT-2 cell-killing assay (Montefiori et al., "Evaluation of Antiviral Drugs and Neutralizing Antibodies to Human Immunodeficiency Virus By a Rapid and Sensitive Microtiter Infection Assay," *J Clin Microbiol.* 26(2):2310-235 (1988), which is hereby incorporated by reference in its entirety). HIV-1$_{IIIB}$ and HIV-1 M$_N$ induce the formation of syncytia in MT-2 cells. The inhibition of the formation of syncytia by the sera shows the activity of neutralizing antibodies present within the sera, induced by vaccination. Immunized test and control sera can be exposed to virus-infected cells (e.g. cells of the MT-2 cell line). Neutralization can be measured by any method that determines viable cells, such as staining, e.g., with Finter's neutral red. Percentage protection can be determined by calculating the difference in absorption between test wells (cells+virus) and dividing this result by the difference in absorption between cell control wells (cells only) and virus control wells (virus only). Neutralizing titers may be expressed, for example, as the reciprocal of the plasma dilution required to protect at least 50% of cells from virus-induced killing.

Another aspect of the present invention relates to a method of inducing a protective and non-neutralizing antibody response against a V2 epitope of HIV-1 gp120 in a subject. This method comprises administering to the subject the isolated immunogenic peptides or polypeptides, as described above, under conditions effective to induce, in the subject, a protective, non-neutralizing antibody response against the V2 epitope of the HIV-1 gp120. In a further embodiment of this aspect of the invention, an HIV-1 positive subject is selected for administration of the isolated immunogenic peptides or polypeptides.

In carrying out this aspect of the present invention, the above-described modes of administering and formulating can be used.

In accordance with this aspect of the present invention, non-neutralizing antibodies will not impair virus entry into cells. However, a non-neutralizing antibody response will trigger antibody-dependent cell-mediated viral inhibition (ADCVI), which may be effective against HIV-1 (Asmal et al., "Antibody Dependent Cell Mediated Viral Inhibition Emerges After Simian Immunodeficiency Virus SIVmac251 Infection of Rhesus Monkeys Coincident With gp140-Binding Antibodies and is Effective Against Neutralization Resistant Viruses," *J. Virol.* 85(11) 5465-5475 (2011), which is hereby incorporated by reference in its entirety).

ADCVI can be measured by infecting polybrene-treated CEM.NKR-CCR5 cells (National Institutes of Health AIDS Research and Reference Program) with a clinical strain of HIV-1 (HIV-$1_{92US657}$). The addition of effector cells from healthy donors and sera from vaccine subjects to the infected target cells can lead to ADCVI. Levels of p24, as determined by ELISA can determine the presence of ADCVI (Forthal et al., "Recombinant gp120 Vaccine-Induced Antibodies Inhibit Clinical Strains of HIV-1 in the Presence of Fc Receptor Bearing Effector Cells and Correlate Inversely with HIV Infection Rate," *J. Immunol.* 178(10): 6596-6603 (2007), which is hereby incorporated by reference in its entirety).

Another aspect of the present invention relates to a method of inducing protective antibodies against a V2 epitope of HIV-1 gp120 in a subject. This method comprises administering to the subject the isolated immunogenic peptides or polypeptides, as described above, under conditions effective to induce, in the subject, a protective antibody response against the V2 epitope of the HIV-1 gp120. In a further embodiment, an HIV-1 positive subject is selected for administration of the isolated immunogenic peptides or polypeptides.

In carrying out this aspect of the present invention, the above-described modes of administering and formulating can be used.

The presence of a protective humoral immunological response can be determined and monitored by testing a biological sample (e.g., blood, plasma, serum, urine, saliva, feces, CSF or lymph fluid) from the subject for the presence of antibodies directed to the immunogenic component of the administered pharmaceutical composition.

The immunization protocol preferably includes at least one priming dose, followed by one or multiple boosting doses administered over time. An exemplary range for an immunogenically effective amount of the present immunogenic polypeptides is about 5 to about 500 µg/kg body weight. A preferred range is about 10-100 µg/kg.

The present invention is further directed to an isolated antibody raised against the isolated immunogenic peptides or polypeptides of the present invention. The isolated antibody of the present invention encompasses any immunoglobulin molecule that specifically binds the V2 epitope of HIV-1 gp120. As used herein, the term "antibody" is meant to include intact immunoglobulins derived from natural sources or from recombinant sources, as well as immunoreactive portions (i.e., antigen binding portions) of intact immunoglobulins. The antibodies of the present invention may exist in a variety of forms including, for example, polyclonal antibodies, monoclonal antibodies, intracellular antibodies ("intrabodies"), antibody fragments (e.g. Fv, Fab and F(ab)2), as well as single chain antibodies (scFv), chimeric antibodies and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli*," *Proc Natl Acad Sci USA* 85:5879-5883 (1988); Bird et al, "Single-Chain Antigen-Binding Proteins," *Science* 242:423-426 (1988), each of which is hereby incorporated by reference in its entirety).

Antibodies of the present invention may also be synthetic antibodies. A synthetic antibody is an antibody which is generated using recombinant DNA technology, such as, for example, an antibody expressed by a bacteriophage. Alternatively, the synthetic antibody is generated by the synthesis of a DNA molecule encoding and expressing the antibody of the present invention or the synthesis of an amino acid specifying the antibody, where the DNA or amino acid sequence has been obtained using synthetic DNA or amino acid sequence technology which is available and well known in the art.

Methods for monoclonal antibody production may be carried out using the techniques described herein or other well-known in the art (MONOCLONAL ANTIBODIES-PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest (i.e., a polymerized first or second peptide or fusion peptide) either in vivo or in vitro.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur. J. Immunol.* 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

Alternatively monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries (McCafferty et al., "Phage Antibodies: Filamentous Phage Displaying Antibody Variable Domains," *Nature* 348: 552-554 (1990); Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety).

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

The monoclonal antibody of the present invention can be a humanized antibody. Humanized antibodies are antibodies that contain minimal sequences from non-human (e.g., murine) antibodies within the variable regions. Such antibodies are used therapeutically to reduce antigenicity and human anti-mouse antibody responses when administered to a human subject. In practice, humanized antibodies are typically human antibodies with minimal to no non-human sequences. A human antibody is an antibody produced by a human or an antibody having an amino acid sequence corresponding to an antibody produced by a human.

Procedures for raising polyclonal antibodies are also well known. Typically, such antibodies can be raised by administering the peptide or polypeptide containing the epitope of interest (i.e. polymerized first or second peptides or fusion peptides) subcutaneously to rabbits (e.g. New Zealand white rabbits), goats, sheep, swine or donkeys which have been bled to obtain pre-immune serum. The antigens can be injected in combination with an adjuvant. The rabbits are bled approximately every two weeks after the first injection and periodically boosted with the same antigen three times every six weeks. Polyclonal antibodies are recovered from the serum by affinity chromatography using the corresponding antigen to capture the antibody. This and other procedures for raising polyclonal antibodies are disclosed in Ed Harlow and David Lane, USING ANTIBODIES: A LABORATORY MANUAL (Cold Spring Harbor Laboratory Press, 1988), which is hereby incorporated by reference in its entirety.

In addition to whole antibodies, the present invention encompasses binding portions of such antibodies. Such binding portions include the monovalent Fab fragments, Fv fragments (e.g., single-chain antibody, scFv), and single variable $V_H$ and $V_L$ domains, and the bivalent F(ab')$_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES:PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

It may further be desirable, especially in the case of antibody fragments, to modify the antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Antibody mimics are also suitable for use in accordance with the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J. Mol. Biol.* 284:1141-1151 (1998); Koide et al., "Probing Protein Conformational Changes in Living Cells by Using Designer Binding Proteins: Application to the Estrogen Receptor," *Proc. Natl. Acad. Sci. USA* 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol.* 15(8):772-777 (1997), which is hereby incorporated by reference in its entirety).

The present invention is further directed to a method of detecting whether a subject is infected with HIV-1. This method includes providing a sample from the subject. The sample is contacted with the isolated immunogenic peptide described above under conditions effective to cause an immunogenic reaction between antibodies in the sample and the immunogenic peptide chimera. Any subject, where the contacting results in the immunogenic reaction, is identified as being infected with HIV-1.

The diagnosis of HIV-1 is based on the detection of V2-specific antibodies in the subject. The presence of antibodies reactive with the V2-specific peptides can be detected using standard electrophoretic and immunodiagnostic techniques, including immunoassays such as competition, direct reaction, or sandwich type assays. Such assays include, but are not limited to: western blots; agglutination tests; enzyme-labeled and mediated immunoassays, such as ELISAs; biotin/avidin type assays; radioimmunoassays; immunoelectrophoresis; immunoprecipitation, etc. The reactions generally involve using labels such as fluorescent, chemiluminescent, radioactive, or enzymatic labels or dye molecules, or other methods for detecting the formation of a complex between the antigen and the antibody.

EXAMPLES

The following examples are provided to illustrate embodiments of the present invention but they are by no means intended to limit its scope.

Example 1—Anti-V2 Antibodies are Associated with Increased Protection from HIV Infection The RV144 case-control study was specifically designed to correlate protection from HIV infection with vaccine-induced immune factors (Haynes et al., "Immune-Correlates Analysis of an HIV-1 Vaccine Efficacy Trial," *NEJM* 366: 1275-1286 (2012), which is hereby incorporated by reference in its entirety). More than 270 assays were performed for the RV144 immune correlates case-control study. Of these, only three, ELISAs of serum antibody (Ab) reactivity with a gp70-V1V2 domain fusion protein, a V2 loop MN strain peptide, and a V2 loop microarray, were associated with an odds ratio (OR) of less than 0.6 of being infected with HIV. Thus, only these three detected a molecular entity, high levels of which was significantly associated with low levels of infection: all three detected vaccine-elicited Abs that directly led to protection (the low OR suggests that these molecules directly blocked infecting viruses; these are the only three assays to detect such molecules, as the only other protection-associated OR was a HIGH OR for plasma IgA, which can only be explained by indirect mechanisms). Thus, current data indicate that anti-V2 Abs are the best supported molecular entities to be associated with direct protection from HIV infection. Interestingly, protection against neutralization-resistant viruses was also recently correlated with anti-V2 Abs in a non-human primate (NHP) model (Barouch et al., "Vaccine Protection Against Acquisition of Neutralization-Resistant SIV Challenges in Rhesus Monkeys," *Nature* 482: 89-93 (2012), which is hereby incorporated by reference in its entirety).

Alignment of the key V2 detection reagents of all three low-OR assays shows that the commonality between them is the peptide region extending from position 165 to position 181 of the V2 loop (FIG. 1). Interestingly, a recent sieve analysis of the RV144 data independently found only two amino acid positions in the HIV genome that were statistically associated with vaccine efficacy and both positions are within the same common region identified in FIG. 1 (positions 169 and positions 181) (Rolland et al., "HIV-1 Vaccine Efficacy Against Viruses With Genetic Signatures in Env V2," *Nature* 490: 417-420 (2012), which is hereby incorporated by reference in its entirety). Thus, integration of all the detailed protection data from the RV144 trial points to Abs elicited by the ALVAC-AIDSVAX vaccine targeting the peptide segment from 165-181 of the V2 loop ($V2^{165-181}$) as being associated with protection.

Figure 2:
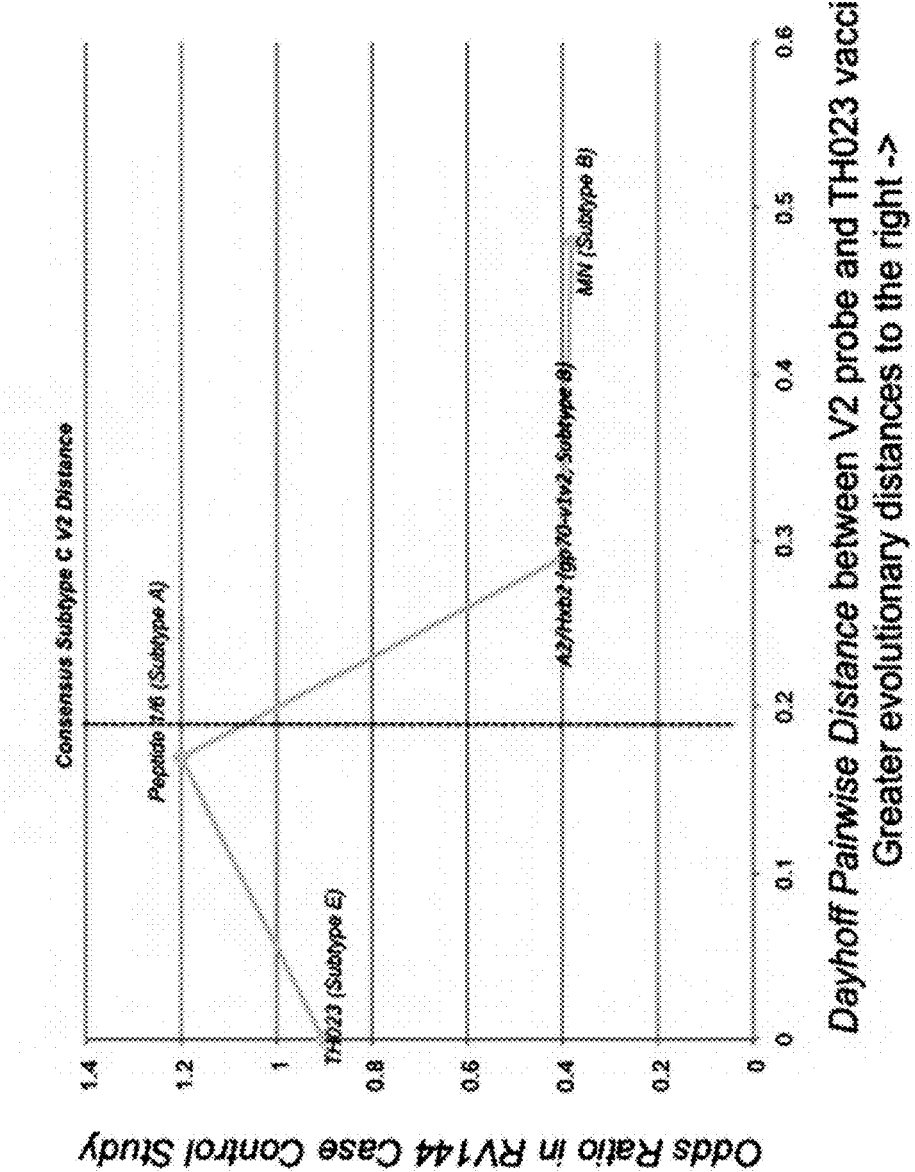
FIG. 2 shows protective antibodies need to be elicited by the subtype AE strain TH023 and yet cross react with subtype B strains. Plotting the odds ratio (OR) (Y-axis) of diverse V2 loop peptides tested in the RV144 case-control study against the evolutionary distance of each peptide from the TH023 immunogen (X-axis) shows that protection (low OR) only appears at the distance of subtype B. The vaccine-elicited antibodies must derive at least partly from the subtype AE immunogen because AIDSVAX B/E alone did not protect in the Vaxgen study, and the only difference in the RV144 study was the addition of the ALVAC priming vector expressing a subtype AE gp120 immunogen. Thus, only those antibodies elicited from subtype AE but cross-reacting with evolutionary distant subtype B strains were associated with protection. Antibodies that cross reacted with less distant heterologous viruses (e.g. subtype A) were not associated with protection. A related finding by Zolla-Pazner et al., "Vaccine-Induced IgG Antibodies to V1V2 Regions of Multiple HIV-1 Subtypes Correlate with Decreased Risk of HIV-1 Infection," *PLoS ONE* 9(2): e87572 (2014), which is hereby incorporated by reference in its entirety, is that the protective antibodies from the RV144 trial cross react with whole V1V2 domains from multiple HIV-1 subtypes from AE to B. Thus, a critical molecular feature of certain HIV-protective antibodies from the RV144 trial, in addition to their targeting of a peptide epitope in $V2^{165-181}$, is that they cross-react between HIV subtypes AE and B, at least, and at most, cross-react with all subtypes. More specifically, they cross-react with the isolated V1V2 domains scaffolded on the non-HIV gp70 protein from HIV subtypes AE and B, at least, and at most, all subtypes.

Example 2—Specific Features of Protective, $V2^{165-181}$-Targeted Antibodies $V2^{165-181}$ corresponds to the "C" β-strand in the published crystal structure of the V1V2 domain and flanking loops (FIG. 1). In a 3D model of the unliganded gp120 trimer based on recent cryo-EM and crystallographic structures (FIG. 5), this segment is exposed at the edge of the unliganded gp120 trimer. The inferred, protective, $V2^{165-181}$-targeted Abs are, therefore, likely to bind to amino acids in this β-strand and flanking loops. At least one species of the epitope targeted by the protective Ab does not include glycans, because two of the reagents displayed in FIG. 1, the V2 peptide from the MN strain and the V2 hotspot array, are pure, chemically synthesized peptides. Also, there are no common glycosylation sites within $V2^{165-181}$ in circulating V2 loops. In addition, a plot of the OR of various V2 sequences used in the RV144 case control analysis versus their evolutionary distance from the vaccine immunogen (FIG. 2) shows that Abs elicited by the subtype AE vaccine immunogen need to be cross-reactive across the evolutionary distance from subtype AE to subtype B in order to be protective. Specifically, the protective Abs may be identified by their cross reactivity between HIV strain TH023/A244, from which the Abs were likely elicited since this was present in both the RV144 vaccine prime and boost, and HIV strain MN. Abs that cross react with heterologous V2 loops only as far as subtype A or C would not have been protective (FIG. 2). While a requirement for this level of cross reactivity has been previously theorized in general for HIV vaccines, here it is derived directly from RV144 case control data as necessary for protection. Thus, specific features of at least one type of protective anti-$V2^{165-181}$ Ab can, therefore, be inferred from the RV144 case control study: the Ab a) binds the "C" β-strand of the V1V2 domain, b) binds amino acids only, not glycans, and c) cross reacts with viruses bearing the subtype AE TH023 strain V2 loop sequence and with viruses bearing the subtype B MN and Hxbc2/A2 strain V2 loop sequences.

Example 3—$V2^{165-181}$ is Immunogenic in Mice and Humans

Figure 3:
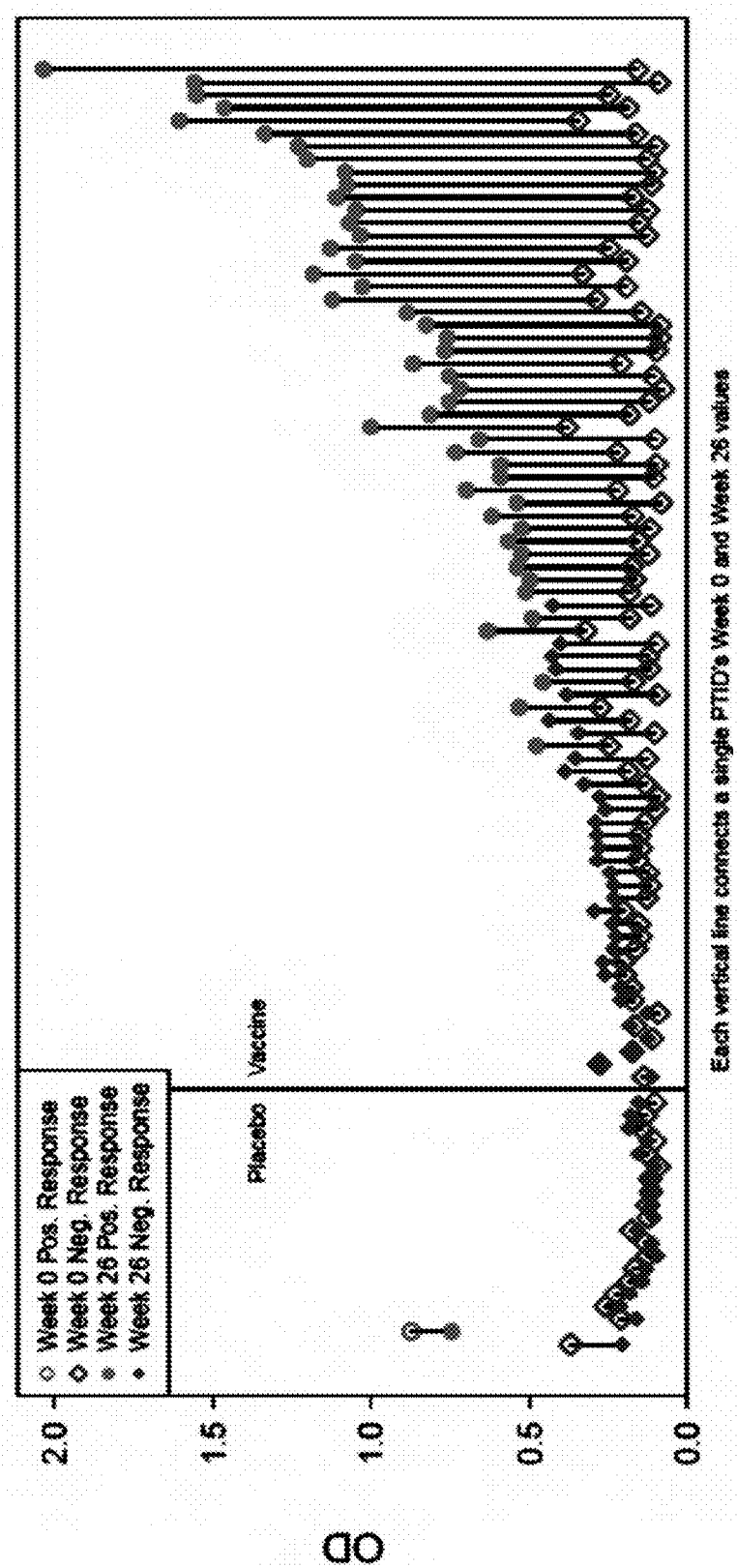
FIG. 3 shows $V2^{165-181}$ is immunogenic in non-HIV-infected human subjects. Shown is a vertical line plot of ELISA optical densities measuring reactivity of individual RV144 patient serum with a biotinylated $V2^{165-185}$ peptide. Reactivity of patient serum at week 0 of vaccination is shown with the open circles (positive response) and open diamonds (negative response). Reactivity of the patient serum at week 26 after vaccination is shown with filled red circles (statistically significant positive response) or filled blue diamonds (statistically insignificant or negative response). Patients receiving the placebo are plotted left of the black line, patients receiving the RV144 vaccine are plotted in increasing order of reactivity gap to the right of the black line. The $V2^{165-185}$ peptide reacts specifically with vaccinated patients and only at week 26 after vaccination in the majority of subjects. Data included with permission from the Military Health Research Program (MHRP) of the Armed Forces, who conducted the RV144 vaccine trial.

The identification of a specific epitope region associated with protection is a tremendous opportunity to advance HIV vaccine research. However, the ability to elicit Abs targeted at this region with the desired molecular properties is the major challenge to taking advantage of this opportunity. Many broadly neutralizing monoclonal antibodies (mAbs) have been isolated, but none have been elicited. Nevertheless, Abs can be readily elicited from naturally immunogenic peptide regions of gp120, and they can potentially be immunofocused to exhibit desired properties (Zolla-Pazner et al., "Structure-Function Relationships of HIV-1 Envelope Sequence-Variable Regions Refocus Vaccine Design," *Nature Rev. Immunol.* 10: 527-535 (2010); Zolla-Pazner et al., "Cross-*Clade* HIV-1 Neutralizing Antibodies Induced With V3-Scaffold Protein Immunogens Following priming with gp120 DNA," *J. Virol.* 85: 9887-9898 (2011), each of which is hereby incorporated by reference in its entirety). So, is $V2^{165-181}$ naturally immunogenic? The answer is yes, in humans and mice. First, a human mAb isolated from an HIV-infected subject, PG-9, is already known to target the V2 C β-strand (FIG. 1 and McLellan et al., "Structure of HIV-1 gp120 V1N2 Domain With Broadly Neutralizing Antibody PG9," *Nature* 480: 336-343 (2011); Walket er al., "Broad and Potent Neutralizing Antibodies From an African Donor Reveal a New HIV-1 Vaccine Target," *Science* 326: 285-289 (2009), each of which is hereby incorporated by reference in its entirety). Thus, the human immune system can, at least under some conditions, generate Abs targeting the C β-strand. Second, 8 out of 9 mAbs isolated from mice immunized with recombinant gp120 from strain MN (one of the RV144 immunogens) target the $V2^{165-181}$ segment (Nakamura et al., "Monoclonal Antibodies to the V2 Domain of MN-rgp120: Fine Mapping of Epitopes and Inhibition of alpha4beta7 Binding," *PLoS One* 7: e39045 (2012), which is hereby incorporated by reference in its entirety). Finally, preliminary work clearly maps the specificity of RV144 vaccine anti-V2 Abs to the $V2^{165-185}$ segment (FIG. 3). Specifically, diverse V2 peptides were selected for testing on the basis of chemical diversity rather than phylogeny. As a result, a $V2^{165-185}$ peptide was found to be strongly and specifically reactive with RV144 vaccine serum and not with placebo subject serum. Thus, multiple lines of evidence suggest that $V2^{165-181}$ is naturally immunogenic in humans and in mammalian animal models.

Example 4—Immunofocusing to $V2^{165-181}$

Figure 4A:
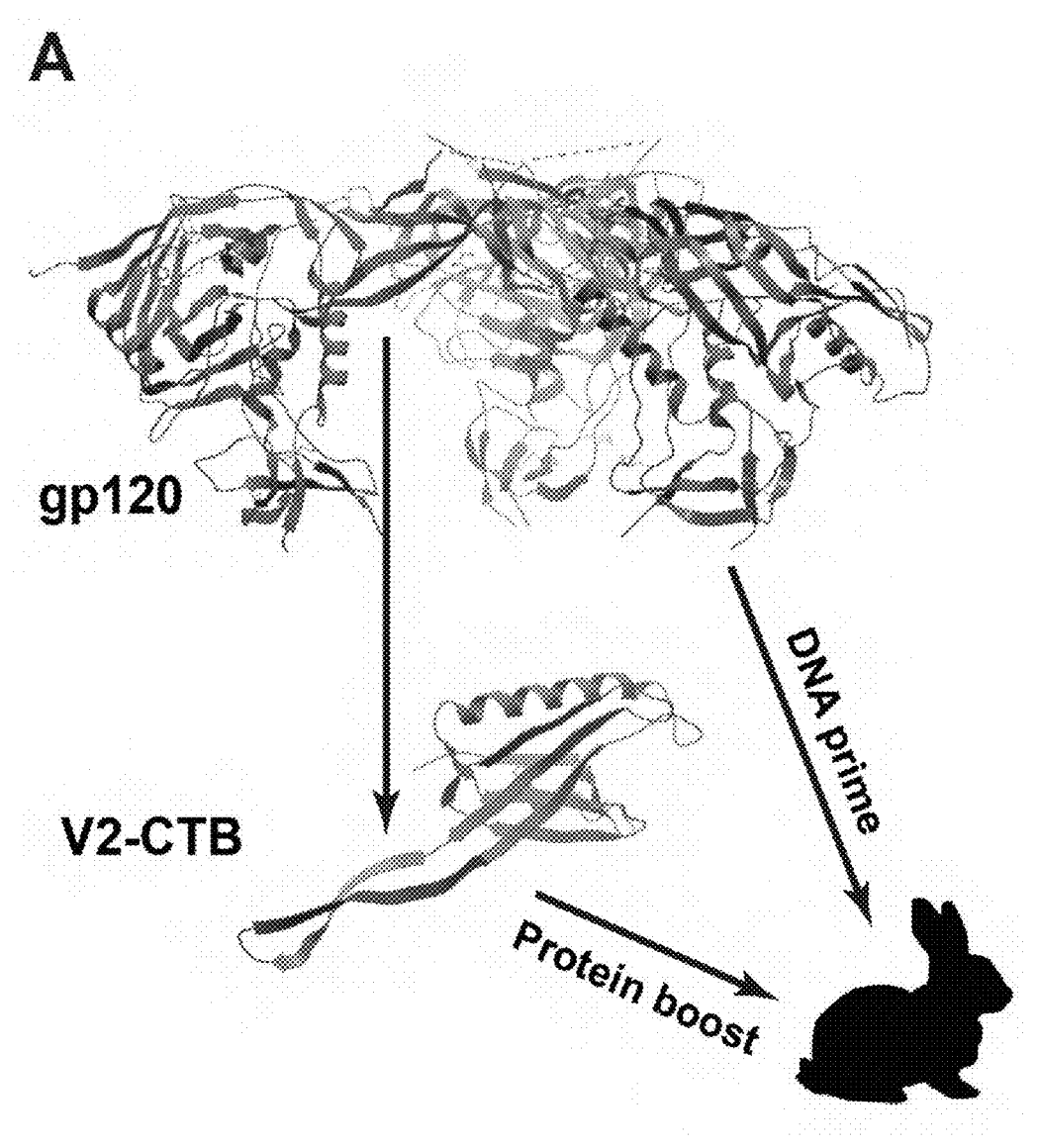
Figures 4B, 4C:
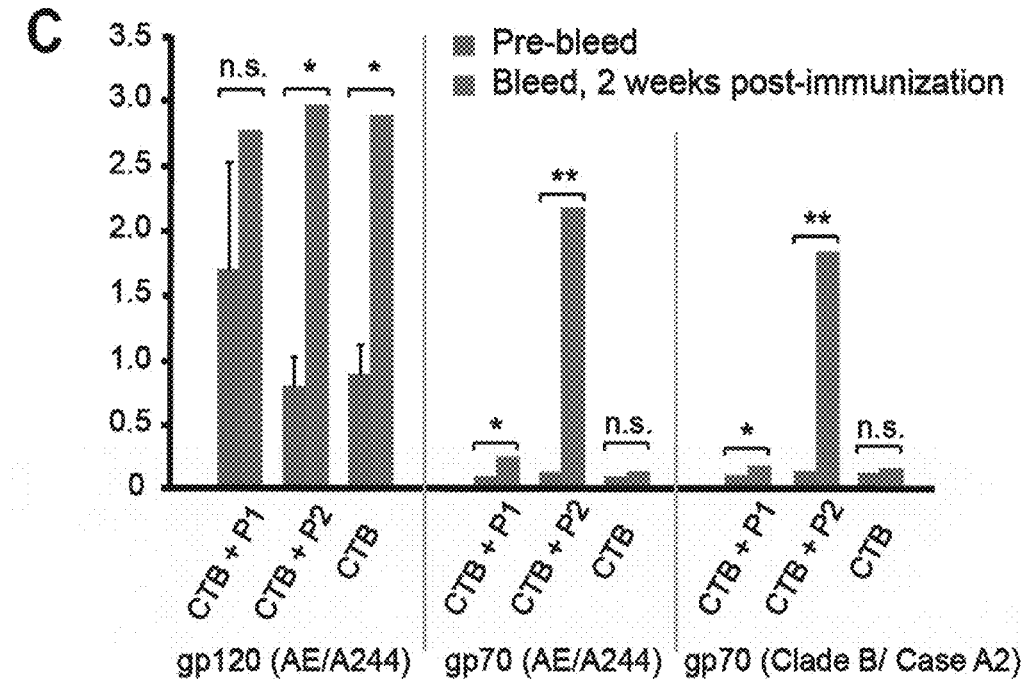

The immunofocusing platform can exclusively focus to $V2^{165-181}$ (FIG. 4). The boundaries of the $V2^{165-181}$ insert and the baseline stability and immunogenicity of the immunogen was determined in this step. From this starting point, it is possible to vary the $V2^{165-181}$ insert sequence to potently and precisely immunofocus to specific $V2^{165-181}$ epitopes.

Figure 5:
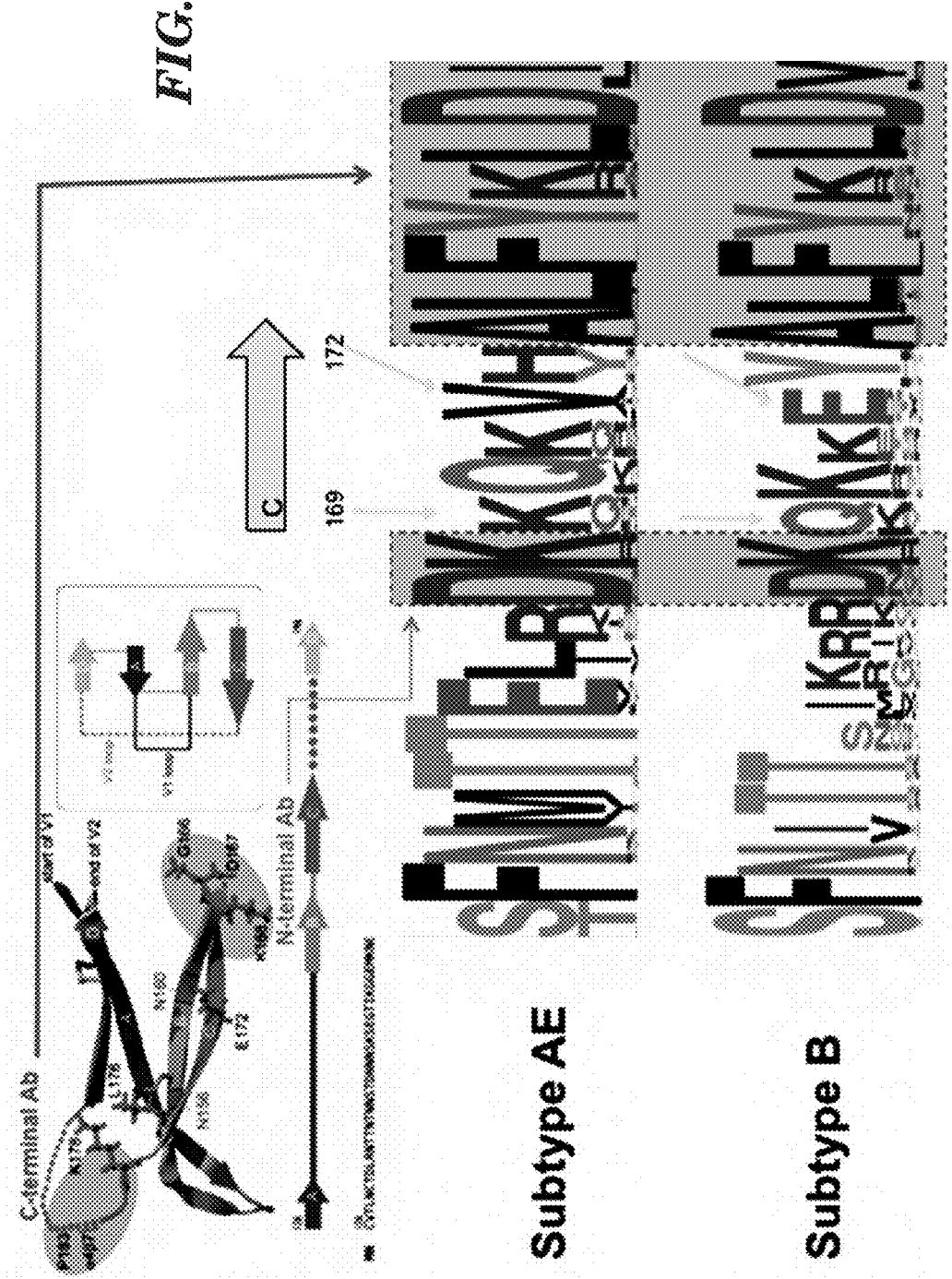
FIG. 5 shows conserved amino acids for different anti-V2$^{165-181}$ antibodies. It is hypothesized that the antibodies cross-react between AE and B, so they are specific for amino acids conserved between these subtypes. In the upper left panel is the model of the V1V2 domain with mouse mAb specificity locations indicated as grey ovals (Figure adapted from Nakamura et al., "Monoclonal Antibodies to the V2 Domain of MN-rgp120: Fine Mapping of Epitopes and Inhibition of alpha4beta7 Binding," *PLoS One* 7: e39045 (2012), which is hereby incorporated by reference in its entirety). Note that they are not specific to the C strand. Two conserved blocks are evident between subtypes AE and B V2s (shaded in web logo at the bottom). It is hypothesized that antibodies may be specific for either the N-terminal or C-terminal block based on Nakamura et al., "Monoclonal Antibodies to the V2 Domain of MN-rgp120: Fine Mapping of Epitopes and Inhibition of alpha4beta7 Binding," *PLoS One* 7: e39045 (2012), which is hereby incorporated by reference in its entirety. Position 169 is labeled with an arrow: a K at this position was correlated with vaccine efficacy, and K is moderately conserved between the subtypes.
Figure 6:
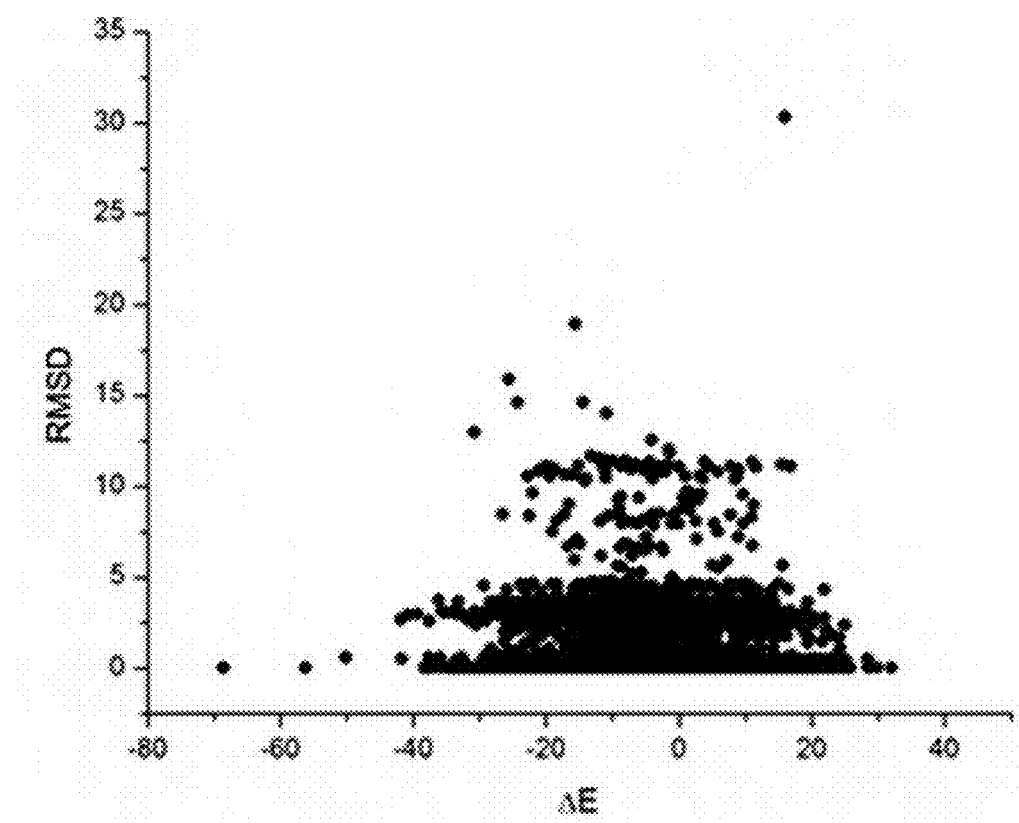
FIG. 6 shows structural fit of V2$^{165-181}$ sequences to V1V2 3D domain structure distinguishes "bad" from "good" sequences. All V2$^{165-181}$ sequences from LANL were modeled onto the V1V2 domain structure and the van der Waals and electrostatic energy of the fit model calculated (X-axis) and plotted vs. the RMSD of fit to 3D domain. <2% of sequences fit more than 5A RMSD (circle) and they are artifactual.

Example 5—Design of Immunogens That Elicit Serum Antibodies in Mammals Targeting $V2^{165-181}$ The goal is to rationally alter the sequence of the insert in CTB-$V2^{165-181}$ to focus the elicitation response from the immunogen on conserved amino acid clusters at the periphery of the C β-strand (FIG. 5). CTB-$V2^{165-181}$ design steps require 3D structural analysis of the candidate sequences to ensure that native $V2^{165-181}$ conformations are retained, and the immunogen production steps require basic biochemical procedures of protein expression and purification. Homology models were made of all naturally occurring $V2^{165-181}$ sequences threaded onto the crystallographic 3D structure of the V1V2 domain. A composite energy score for the fit of each sequence to the structure, including van der Waals, electrostatics and backbone torsion energy, was calculated. Most naturally occurring sequences fit well to the structure suggesting that most adopt the same structural fold (FIG. 6). A small number of artifactual sequences show poor energy scores. This method was used to select the FIG. 4 antigenic sequence. Thus, modeling candidate antigen sequences onto the 3D structure of the V1V2 domain can rapidly determine if they are consistent with the $V2^{165-181}$ β-hairpin conformation.

The immunogen consists of the CTB protein with a variable sequence inserted as a loop at the location shown in FIG. 4A. Only the inserted sequence is designed, the CTB sequence and joining sequences are not altered. The design method attempts to minimize the charge and volume of amino acid side chains that are NOT targeted for elicitation. Each non-targeted amino acid is changed to the most similar amino acid with a smaller hydrophobic volume or a lesser electrostatic charge. Prior studies have suggested that these changes redirect the Ab response towards the backbone or away from alternative mAb epitopes (e.g. FIG. 4A). The resulting synthetic sequence is then modeled to determine if it continues to favor the native $V2^{165-181}$ backbone conformation.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated immunogenic peptide consisting of the amino acid sequence corresponding to SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

2. An immunogenic vaccine composition comprising:
   the isolated immunogenic polypeptide of claim 1 and
   an immunologically and pharmaceutically acceptable vehicle or excipient.

3. The isolated immunogenic peptide of claim 1, wherein the isolated immunogenic peptide consists of the amino acid sequence corresponding to SEQ ID NO: 16.

4. The isolated immunogenic peptide of claim 1, wherein the isolated immunogenic peptide consists of the amino acid sequence corresponding to SEQ ID NO: 17.

5. The isolated immunogenic peptide of claim 1, wherein the isolated immunogenic peptide consists of the amino acid sequence corresponding to SEQ ID NO: 18.

6. The isolated immunogenic peptide of claim 1, wherein the isolated immunogenic peptide consists of the amino acid sequence corresponding to SEQ ID NO: 19.

7. The isolated immunogenic peptide of claim 1, wherein the isolated immunogenic peptide consists of the amino acid sequence corresponding to SEQ ID NO: 20.

8. The isolated immunogenic peptide of claim 1, wherein the isolated immunogenic peptide consists of the amino acid sequence corresponding to SEQ ID NO: 21.

9. The isolated immunogenic peptide of claim 1, wherein the isolated immunogenic peptide consists of the amino acid sequence corresponding to SEQ ID NO: 22.

10. The isolated immunogenic peptide of claim 1, wherein the isolated immunogenic peptide consists of the amino acid sequence corresponding to SEQ ID NO: 23.

11. The isolated immunogenic peptide of claim 1, wherein the isolated immunogenic peptide consists of the amino acid sequence corresponding to SEQ ID NO: 24.

* * * * *

SEQUENCE LISTING

<160> NUMBER OF SEQ ID NOS: 24

<210> SEQ ID NO 1
<211> LENGTH: 16
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: X is K, R, T, Q or E
<220> FEATURE:
<221> NAME/KEY: MISC_FEATURE
<222> LOCATION: (2)..(2)
<223> OTHER INFORMATION: X is Q, K, R, V, T, M, I, L, F, or E
<220> FEATURE:
<221> NAME/KEY: MISC_FEATURE
<222> LOCATION: (3)..(3)
<223> OTHER INFORMATION: X is Q, K, R, V, E, T or H
<220> FEATURE:
<221> NAME/KEY: MISC_FEATURE
<222> LOCATION: (4)..(4)
<223> OTHER INFORMATION: X is K, Q, R, N, T, E, or I
<220> FEATURE:
<221> NAME/KEY: MISC_FEATURE
<222> LOCATION: (5)..(5)
<223> OTHER INFORMATION: X is V,A, I, E, D, Q, T, N, F, K, or G
<220> FEATURE:
<221> NAME/KEY: MISC_FEATURE
<222> LOCATION: (6)..(6)
<223> OTHER INFORMATION: X is Y, H, R, N, S, Q, or F
<220> FEATURE:
<221> NAME/KEY: MISC_FEATURE
<222> LOCATION: (7)..(7)
<223> OTHER INFORMATION: X is A, S, or T
<220> FEATURE:
<221> NAME/KEY: MISC_FEATURE
<222> LOCATION: (8)..(8)
<223> OTHER INFORMATION: X is L, I, F, T, Y, or V
<220> FEATURE:
<221> NAME/KEY: MISC_FEATURE
<222> LOCATION: (9)..(9)
<223> OTHER INFORMATION: X is F, L, or T
<220> FEATURE:
<221> NAME/KEY: MISC_FEATURE
<222> LOCATION: (10)..(10)
<223> OTHER INFORMATION: X is Y, N, H, D, S, or V
<220> FEATURE:
<221> NAME/KEY: MISC_FEATURE
<222> LOCATION: (11)..(11)
<223> OTHER INFORMATION: X is K, R, T, M, N, S, E, Q, V, or A
<220> FEATURE:
<221> NAME/KEY: MISC_FEATURE
<222> LOCATION: (12)..(12)
<223> OTHER INFORMATION: X is L, P, Y, S, I, F, V, T, H, or G
<220> FEATURE:
<221> NAME/KEY: MISC_FEATURE
<222> LOCATION: (13)..(13)
<223> OTHER INFORMATION: X is D, N, E, or V
<220> FEATURE:
<221> NAME/KEY: MISC_FEATURE
<222> LOCATION: (14)..(14)
<223> OTHER INFORMATION: X is V, I, T, or L
<220> FEATURE:
<221> NAME/KEY: MISC_FEATURE
<222> LOCATION: (15)..(15)
<223> OTHER INFORMATION: X is V, I, E, T, M, or A
<220> FEATURE:
<221> NAME/KEY: MISC_FEATURE
<222> LOCATION: (16)..(16)
<223> OTHER INFORMATION: X is Q, P, S, K, E, R, or A

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

```
<210> SEQ ID NO 2
<211> LENGTH: 11
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: X is R, K, S, I, M, T, or Q
<220> FEATURE:
<221> NAME/KEY: MISC_FEATURE
<222> LOCATION: (2)..(2)
<223> OTHER INFORMATION: X is N, K, or C
<220> FEATURE:
<221> NAME/KEY: MISC_FEATURE
<222> LOCATION: (3)..(3)
<223> OTHER INFORMATION: X is C ,N, R, or F
<220> FEATURE:
<221> NAME/KEY: MISC_FEATURE
<222> LOCATION: (4)..(4)
<223> OTHER INFORMATION: X is T, C, or S
<220> FEATURE:
<221> NAME/KEY: MISC_FEATURE
<222> LOCATION: (5)..(5)
<223> OTHER INFORMATION: X is F or S
<220> FEATURE:
<221> NAME/KEY: MISC_FEATURE
<222> LOCATION: (6)..(6)
<223> OTHER INFORMATION: X is N, K, F, S, D, or Y
<220> FEATURE:
<221> NAME/KEY: MISC_FEATURE
<222> LOCATION: (7)..(7)
<223> OTHER INFORMATION: X is M, V, I, N, T, or A
<220> FEATURE:
<221> NAME/KEY: MISC_FEATURE
<222> LOCATION: (8)..(8)
<223> OTHER INFORMATION: X is T, I, S, V, or A
<220> FEATURE:
<221> NAME/KEY: MISC_FEATURE
<222> LOCATION: (9)..(9)
<223> OTHER INFORMATION: X is T, S, A, P, or G
<220> FEATURE:
<221> NAME/KEY: MISC_FEATURE
<222> LOCATION: (10)..(10)
<223> OTHER INFORMATION: X is E, V, L, S, N, T, G, D, E, R, I, V, A,
      or P
<220> FEATURE:
<221> NAME/KEY: MISC_FEATURE
<222> LOCATION: (11)..(11)
<223> OTHER INFORMATION: X is L, I, V, M, S, R, T, or N

<400> SEQUENCE: 2

Xaa Xaa Xaa Xaa Xaa Xaa Xaa Xaa Xaa Xaa Xaa
1               5                   10

<210> SEQ ID NO 3
<211> LENGTH: 15
<212> TYPE: PRT
<213> ORGANISM: Artificial
<220> FEATURE:
<223> OTHER INFORMATION: peptide

<400> SEQUENCE: 3

Lys Met Gln Lys Val Tyr Ala Leu Thr Tyr Lys Leu Asp Ile Val
1               5                   10                  15

<210> SEQ ID NO 4
<211> LENGTH: 15
<212> TYPE: PRT
<213> ORGANISM: Artificial
<220> FEATURE:
<223> OTHER INFORMATION: peptide
```

```
<400> SEQUENCE: 4

Lys Ile Gln Ile Val Tyr Ala Leu Phe Tyr Gln Leu Asp Ile Val
1               5                   10                  15

<210> SEQ ID NO 5
<211> LENGTH: 6
<212> TYPE: PRT
<213> ORGANISM: Artificial
<220> FEATURE:
<223> OTHER INFORMATION: peptide

<400> SEQUENCE: 5

Ser Phe Asn Ile Thr Gly
1               5

<210> SEQ ID NO 6
<211> LENGTH: 23
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: X is R, K, S, I, M, T, or Q
<220> FEATURE:
<221> NAME/KEY: MISC_FEATURE
<222> LOCATION: (2)..(2)
<223> OTHER INFORMATION: X is N, K, or C
<220> FEATURE:
<221> NAME/KEY: MISC_FEATURE
<222> LOCATION: (3)..(3)
<223> OTHER INFORMATION: X is C, N, R, or F
<220> FEATURE:
<221> NAME/KEY: MISC_FEATURE
<222> LOCATION: (4)..(4)
<223> OTHER INFORMATION: X is S, T, or C
<220> FEATURE:
<221> NAME/KEY: MISC_FEATURE
<222> LOCATION: (5)..(5)
<223> OTHER INFORMATION: X is F or S
<220> FEATURE:
<221> NAME/KEY: MISC_FEATURE
<222> LOCATION: (6)..(6)
<223> OTHER INFORMATION: X is N, K, F, S, D, or Y
<220> FEATURE:
<221> NAME/KEY: MISC_FEATURE
<222> LOCATION: (7)..(7)
<223> OTHER INFORMATION: X is M, V, I, N, T, or A
<220> FEATURE:
<221> NAME/KEY: MISC_FEATURE
<222> LOCATION: (8)..(8)
<223> OTHER INFORMATION: X is T, I, S, V, or A
<220> FEATURE:
<221> NAME/KEY: MISC_FEATURE
<222> LOCATION: (9)..(9)
<223> OTHER INFORMATION: X is T, S, A, P, or G
<220> FEATURE:
<221> NAME/KEY: MISC_FEATURE
<222> LOCATION: (10)..(10)
<223> OTHER INFORMATION: X is E, V, L, S, N, T, G, D, E, R, I, V, A,
      or P
<220> FEATURE:
<221> NAME/KEY: MISC_FEATURE
<222> LOCATION: (11)..(11)
<223> OTHER INFORMATION: X is L, I, V, M, S, R, T, or N
<220> FEATURE:
<221> NAME/KEY: MISC_FEATURE
<222> LOCATION: (12)..(12)
<223> OTHER INFORMATION: X is R, K, T, I, Q, S, A, G, or N
<220> FEATURE:
<221> NAME/KEY: MISC_FEATURE
<222> LOCATION: (13)..(13)
<223> OTHER INFORMATION: X is D, N, K, G, or R
<220> FEATURE:
```

```
<221> NAME/KEY: MISC_FEATURE
<222> LOCATION: (14)..(14)
<223> OTHER INFORMATION: X is K, R, T, E, Q, or I
<220> FEATURE:
<221> NAME/KEY: MISC_FEATURE
<222> LOCATION: (15)..(15)
<223> OTHER INFORMATION: X is K, Q, R, T, V, M, I, L, F, or E
<220> FEATURE:
<221> NAME/KEY: MISC_FEATURE
<222> LOCATION: (16)..(16)
<223> OTHER INFORMATION: X is Q, K, R, V, T, E, or H
<220> FEATURE:
<221> NAME/KEY: MISC_FEATURE
<222> LOCATION: (17)..(17)
<223> OTHER INFORMATION: X is K, Q, R, N, T, or E
<220> FEATURE:
<221> NAME/KEY: MISC_FEATURE
<222> LOCATION: (18)..(18)
<223> OTHER INFORMATION: X is V, A, I, E, D, Q, T, N, F, K, or G
<220> FEATURE:
<221> NAME/KEY: MISC_FEATURE
<222> LOCATION: (19)..(19)
<223> OTHER INFORMATION: X is Y, H, R, S, N, Q, or F
<220> FEATURE:
<221> NAME/KEY: MISC_FEATURE
<222> LOCATION: (21)..(21)
<223> OTHER INFORMATION: X is L, I, F, T, Y, or V
<220> FEATURE:
<221> NAME/KEY: MISC_FEATURE
<222> LOCATION: (22)..(22)
<223> OTHER INFORMATION: X is F or L
<220> FEATURE:
<221> NAME/KEY: MISC_FEATURE
<222> LOCATION: (23)..(23)
<223> OTHER INFORMATION: X is Y, N, H, D, or S

<400> SEQUENCE: 6

Xaa Xaa Xaa Xaa Xaa Xaa Xaa Xaa Xaa Xaa Xaa Xaa Xaa Xaa Xaa Xaa
1               5                   10                  15

Xaa Xaa Xaa Ala Xaa Xaa Xaa
            20

<210> SEQ ID NO 7
<211> LENGTH: 15
<212> TYPE: PRT
<213> ORGANISM: Artificial
<220> FEATURE:
<223> OTHER INFORMATION: peptide

<400> SEQUENCE: 7

Ser Phe Asn Ile Thr Thr Ser Ile Gly Asp Lys Met Gln Lys Glu
1               5                   10                  15

<210> SEQ ID NO 8
<211> LENGTH: 15
<212> TYPE: PRT
<213> ORGANISM: Artificial
<220> FEATURE:
<223> OTHER INFORMATION: peptide

<400> SEQUENCE: 8

Ser Phe Asn Met Thr Thr Glu Leu Arg Asp Lys Lys Gln Lys Val
1               5                   10                  15

<210> SEQ ID NO 9
<211> LENGTH: 15
<212> TYPE: PRT
<213> ORGANISM: Artificial
<220> FEATURE:
<223> OTHER INFORMATION: peptide

<400> SEQUENCE: 9
```

```
Ser Phe Asn Ile Thr Thr Ser Ile Gly Asp Lys Met Gln Gln Val
1               5                   10                  15

<210> SEQ ID NO 10
<211> LENGTH: 15
<212> TYPE: PRT
<213> ORGANISM: Artificial
<220> FEATURE:
<223> OTHER INFORMATION: peptide

<400> SEQUENCE: 10

Ser Phe Asn Met Thr Thr Glu Leu Gly Asp Lys Lys Gln Gln Val
1               5                   10                  15

<210> SEQ ID NO 11
<211> LENGTH: 15
<212> TYPE: PRT
<213> ORGANISM: Artificial
<220> FEATURE:
<223> OTHER INFORMATION: peptide

<400> SEQUENCE: 11

Ser Phe Asn Met Thr Thr Glu Leu Gln Asn Gln Lys Gln Gln Val
1               5                   10                  15

<210> SEQ ID NO 12
<211> LENGTH: 15
<212> TYPE: PRT
<213> ORGANISM: Artificial
<220> FEATURE:
<223> OTHER INFORMATION: peptide

<400> SEQUENCE: 12

Ser Phe Asn Ile Thr Thr Ser Leu Gln Asn Lys Lys Gln Gln Val
1               5                   10                  15

<210> SEQ ID NO 13
<211> LENGTH: 27
<212> TYPE: PRT
<213> ORGANISM: Artificial
<220> FEATURE:
<223> OTHER INFORMATION: peptide

<400> SEQUENCE: 13

Ser Asn Asn Thr Thr Glu Ser Ile Asn Ile Gly Pro Asp Lys Lys Gln
1               5                   10                  15

Ala Val Thr Gly Glu Ile Ile Gly Asp Ile Arg
            20                  25

<210> SEQ ID NO 14
<211> LENGTH: 15
<212> TYPE: PRT
<213> ORGANISM: Artificial
<220> FEATURE:
<223> OTHER INFORMATION: peptide

<400> SEQUENCE: 14

Ser Phe Asn Ile Thr Thr Ser Ile Gly Asp Lys Met Gln Lys Val
1               5                   10                  15

<210> SEQ ID NO 15
<211> LENGTH: 17
<212> TYPE: PRT
<213> ORGANISM: Artificial
<220> FEATURE:
<223> OTHER INFORMATION: peptide
```

```
<220> FEATURE:
<221> NAME/KEY: MISC_FEATURE
<222> LOCATION: (1)..(2)
<223> OTHER INFORMATION: X is any natural or unnatural amino acid
<220> FEATURE:
<221> NAME/KEY: MISC_FEATURE
<222> LOCATION: (5)..(9)
<223> OTHER INFORMATION: X is any natural or unnatural amino acid
<220> FEATURE:
<221> NAME/KEY: MISC_FEATURE
<222> LOCATION: (14)..(14)
<223> OTHER INFORMATION: X is any natural or unnatural amino acid
<220> FEATURE:
<221> NAME/KEY: MISC_FEATURE
<222> LOCATION: (17)..(17)
<223> OTHER INFORMATION: X is V or I

<400> SEQUENCE: 15

Xaa Xaa Asp Lys Xaa Xaa Xaa Xaa Xaa Ala Leu Phe Tyr Xaa Leu Asp
1               5                   10                  15

Xaa

<210> SEQ ID NO 16
<211> LENGTH: 14
<212> TYPE: PRT
<213> ORGANISM: Artificial
<220> FEATURE:
<223> OTHER INFORMATION: peptide

<400> SEQUENCE: 16

Asp Lys Tyr Gln Gln Gln Gln Ala Leu Phe Tyr Gln Leu Asp
1               5                   10

<210> SEQ ID NO 17
<211> LENGTH: 14
<212> TYPE: PRT
<213> ORGANISM: Artificial
<220> FEATURE:
<223> OTHER INFORMATION: peptide

<400> SEQUENCE: 17

Asp Lys Met Gln Lys Glu Tyr Ala Leu Leu Tyr Lys Leu Asp
1               5                   10

<210> SEQ ID NO 18
<211> LENGTH: 14
<212> TYPE: PRT
<213> ORGANISM: Artificial
<220> FEATURE:
<223> OTHER INFORMATION: peptide

<400> SEQUENCE: 18

Asp Lys Gln Gln Gln Ser Gln Ala Leu Phe Tyr Gln Leu Asp
1               5                   10

<210> SEQ ID NO 19
<211> LENGTH: 14
<212> TYPE: PRT
<213> ORGANISM: Artificial
<220> FEATURE:
<223> OTHER INFORMATION: peptide

<400> SEQUENCE: 19

Asp Lys Gln Gln Gln Gln Ser Ala Leu Phe Tyr Gln Leu Asp
1               5                   10

<210> SEQ ID NO 20
<211> LENGTH: 14
```

```
<212> TYPE: PRT
<213> ORGANISM: Artificial
<220> FEATURE:
<223> OTHER INFORMATION: peptide

<400> SEQUENCE: 20

Asp Lys Ser Gln Gln Gln Gln Ala Leu Phe Tyr Gln Leu Asp
1               5                   10

<210> SEQ ID NO 21
<211> LENGTH: 14
<212> TYPE: PRT
<213> ORGANISM: Artificial
<220> FEATURE:
<223> OTHER INFORMATION: peptide

<400> SEQUENCE: 21

Asp Lys Gln Gln Gln Gln Gln Ala Leu Phe Tyr Gln Leu Asp
1               5                   10

<210> SEQ ID NO 22
<211> LENGTH: 14
<212> TYPE: PRT
<213> ORGANISM: Artificial
<220> FEATURE:
<223> OTHER INFORMATION: peptide

<400> SEQUENCE: 22

Asp Lys Gln Gln Gln Gln Gln Ala Leu Phe Tyr Ser Leu Asp
1               5                   10

<210> SEQ ID NO 23
<211> LENGTH: 14
<212> TYPE: PRT
<213> ORGANISM: Artificial
<220> FEATURE:
<223> OTHER INFORMATION: peptide

<400> SEQUENCE: 23

Asp Lys Gln Ser Gln Gln Gln Ala Leu Phe Tyr Gln Leu Asp
1               5                   10

<210> SEQ ID NO 24
<211> LENGTH: 14
<212> TYPE: PRT
<213> ORGANISM: Artificial
<220> FEATURE:
<223> OTHER INFORMATION: peptide

<400> SEQUENCE: 24

Asp Lys Gln Gln Ser Gln Gln Ala Leu Phe Tyr Gln Leu Asp
1               5                   10
```